United States Patent
Leslie et al.

(10) Patent No.: US 6,933,412 B2
(45) Date of Patent: Aug. 23, 2005

(54) LOW LOSS HIGH REFRACTIVE INDEX VINYL SULFIDE COMPOUNDS AND METHOD OF MAKING SAME

(75) Inventors: Thomas M. Leslie, Horseheads, NY (US); Helen Samson, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 457 days.

(21) Appl. No.: 10/229,885

(22) Filed: Aug. 27, 2002

(65) Prior Publication Data

US 2004/0044251 A1 Mar. 4, 2004

(51) Int. Cl.$^7$ ................ C07C 321/00; C07C 323/00; C07C 315/00
(52) U.S. Cl. .............. 568/25; 568/24; 568/22; 568/18
(58) Field of Search ............ 568/25, 24, 22, 568/18

(56) References Cited

U.S. PATENT DOCUMENTS 2,832,806 A  *  4/1958  Holly et al. .......... 568/56
2,947,730 A  *  8/1960  Holly et al. .......... 526/289

FOREIGN PATENT DOCUMENTS

JP          02085039          4/1990

OTHER PUBLICATIONS

Amosova et al., Reactivity of Vinylthiohalobenzenes and Synthesis of Polyfunctional compounds based on them, Zhurnal Organicheskoi Khimi (1993), 29 (12), 2416–2421.*

Amosova et al., Synthesis of Thermally Stable Fluorine and Sulfur–Containing Homopolymers and Copolymers of Vinylthiohalobenzenes and Styrene, Chemistry for Sustainable Development (1996), 4(1), 9–14.*

"Reactions of Hexachlorobenzene with Mercaptides", Kulka, et al. J. Org. Chem. vol. 24 235–237 Feb. 1959.

* cited by examiner

*Primary Examiner*—Johann Richter
*Assistant Examiner*—Chukwuma Nwaonicha
(74) *Attorney, Agent, or Firm*—Walter M. Douglas

(57) ABSTRACT

The invention is directed to aromatic vinyl sulfide compounds of general formula $A(-S-CH=CH_2)_z$, wherein z is in the range of 1–4 and A represents highly halogenated and highly halogenated-deuterated phenyl, biphenyl and naphthalene compounds; highly halogenated and highly halogenated-deuterated biphenyl ethers and thioethers; and highly halogenated and highly halogenated-deuterated unsaturated 5- and 6-member heterocyclic ring systems containing carbon and at least one heteroatom selected from the group consisting of nitrogen, oxygen and sulfur. The aromatic vinyl sulfide compounds of the invention can be used to prepare elements and devices suitable for use in optical communications.

20 Claims, No Drawings

LOW LOSS HIGH REFRACTIVE INDEX VINYL SULFIDE COMPOUNDS AND METHOD OF MAKING SAME

FIELD OF THE INVENTION

The invention is directed to novel vinyl sulfide compounds and methods of preparing such compounds. In particular, the invention is directed to novel vinyl sulfide compounds having a highly halogenated "aromatic" group attached directly to the sulfur atom without the presence of an intervening moiety, such as a methylene group.

BACKGROUND OF THE INVENTION

In optical communication systems, messages are transmitted by electromagnetic carrier waves at optical frequencies that are generated by sources such as lasers and light-emitting diodes. One preferred device for routing or guiding waves of optical frequencies from one point to another is an optical waveguide. The operation of an optical waveguide is based on the fact that when a light-transmissive medium is surrounded or otherwise bounded by an outer medium having a lower refractive index, light introduced along the axis of the inner medium substantially parallel to the boundary with the outer medium is highly reflected at the boundary, trapping the light in the light transmissive medium and thus producing a guiding effect between channels. A wide variety of optical devices can be made which incorporate such light guiding structures as the light transmissive elements. Examples, without limitation, include planar optical slab waveguides, channel optical waveguides, rib waveguides, optical couplers, optical splitters, optical switches, optical filters, arrayed waveguide gratings, waveguide Bragg gratings, variable attenuators and the like. For light of a particular frequency, optical waveguides may support a single optical mode or multiple modes, depending on the dimensions of the inner light guiding region and the difference in refractive index between the inner medium and the surrounding outer medium.

Organic polymeric materials can be used to construct optical waveguide and interconnect devices such as those given above. However, whereas single mode optical devices built from planar waveguides made from glass are relatively unaffected by temperature, devices made from organic polymers may show a significant variation of properties with temperature. This is due to the fact that organic polymeric materials have a relatively high thermo-optic coefficient (dn/dT). Consequently, a change in temperature causes the refractive index of an optical device made from a polymeric material to change appreciably. This ability to have a change in polymer refractive index due to a temperature change can be used to make active, thermally tunable or controllable devices incorporating light transmissive elements. One example of a thermally tunable device is a 1×2 switching element activated by the thermo-optic effect. In such a device light from an input waveguide may be switched between two output waveguides by the application of a thermal gradient induced by a resistive heater for which the heating/cooling processes occur over the span of one to several milliseconds.

Most polymeric materials, however, contain carbon-hydrogen bonds, which absorb strongly in the 1550 nm wavelength range that is commonly used in telecommunications applications, causing devices made from such materials to have unacceptably high insertion losses. By lowering the concentration of C—H bonds in a material through replacement of C—H bonds with C-D or C-halogen bonds, it is possible to lower the absorption loss at infrared wavelengths. For example, planar waveguides made from fluorinated polyimides and deuterated or fluorinated polymethacrylates have achieved single mode losses of as little as 0.10 dB/cm at 1300 nm and 0.2 bB/cm at 1550 nm. However, it is relatively difficult to make optical devices from these materials. For example, the processes for making such polymeric waveguides typically includes the use of a reactive ion etching process, which is cumbersome and can cause high waveguide loss due to scattering. In addition, deuteration is not an effective means of reducing loss in the 1550 nm wavelength range. Further, fluorinated polyimides and deuterated or fluorinated polymethacrylates can have higher losses on the order of 0.6 dB/cm in the telecommunications window near 1550 nm. Finally, O—H and N—H bonds which may be present in polyinides and polyacrylates contribute strongly to loss at wavelengths near 1310 nm and 1550 nm.

Consequently, in view of the foregoing problems, new polymerizable compositions are sought in which the presence of O—H and N—H bonds is minimal or absent. Further, in view of the foregoing problems encountered using hydrogenated, deuterated and fluorinated polymeric materials, it is also desirable to find new compositions which will not only minimize absorption losses, but will also have a refractive index as high as or higher than the corresponding hydrogenated or fluorinated materials. Organic materials containing sulfur atoms have been found to generally have a higher refractive index than similar compounds that do not contain sulfur atoms. In addition, it has been found that organic materials containing sulfur and chlorine atoms have the desired high refractive indices desired for optical communications devices while maintaining a low C—H count. In particular, it is desirable to prepare novel aromatic vinyl sulfide compounds in which the aromatic ring is highly halogenated

SUMMARY OF THE INVENTION

The invention is directed to aromatic vinyl sulfide compounds generally represented by the formula A(—S—CH=CH$_2$)$_z$, wherein A represents an aromatic or heterocyclic moiety. In one aspect, it has been found that compounds useful in practicing the invention are those in which A represents highly halogenated, halogenated-deuterated and deuterated phenyl, biphenyl and naphthalene compounds, highly halogenated, halogenated-deuterated and deuterated biphenyl ethers and thioethers, and highly halogenated, halogenated-deuterated and deuterated unsaturated 5- and 6-member heterocyclic ring systems containing carbon and at least one heteroatom selected from the group consisting of nitrogen, oxygen and sulfur. In a further aspect, the aromatic moiety is directly bonded to the vinylic sulfur atom. That is, there are no intervening connecting groups, for example, linking alkyl groups —(CH$_2$)$_x$—.

In another aspect, the invention is directed to the compounds 1,4-bis(ethenylthio)-2,3,5,6-tetrachlorobenzene; 4,4'-bis(ethenylthio)-2,2',3,3',5,5',6,6'-octachlorobiphenyl; nonachlorobiphenyl vinyl sulfide; 4,4'-bis(ethenylthio)-2,2', 3,3',5,5',6,6'-octachlorobiphenyl ether; 4,4'-bis(ethenylthio)-2,2',3,3',5,5',6,6'-octachlorobiphenyl thioether; 1,4-bis (ethenylthio)-2,3,5,6-benzene-d$_4$; phenyl-d$_5$ vinyl sulfide; 4-ethenylthio-2,3,5,6-tetrafluorcholorobenzene; 1,3,5-tris (ethenylthio)-2,4,6-trichlorobenzene, isomers of bis-ethenylthio)-hexafluoranaphalene, isomers of tris (ethenylthio)-pentafluoronapthalene, isomers of tetrakis (ethenylthio)-tetrafluoronapthalene and similar compounds.

In an additional aspect, the invention is directed to the heterocyclic compounds 3,4-bis(ethenylthio)-2,5-dichlorofuran; 2,5-bis(ethenylthio)-2,4-dichlorofuran; 2,3,4,5-tetrakis(ethenylthio)furan; 3,4-bis(ethenylthio)-2,5-dichlorothiophene; 2,5-bis(ethenylthio)-2,4-dichlorothiophene; 2,3,4,5-tetrakis(ethenylthio)thiophene; 4-ethtylenethio-2,6-dichloro-1,3,5-triazine; 2,4,6-tris(ethenylthio)1,3,5-triazine; 2,6-bis(ethenylthio)-3,5-dichloropyrazine; 2,3,5,6-tetrakis(ethenylthio)pyrazine; 4,6-bis(ethenylthio)-2,5-dichloropyrimidine; 2,4,6-tris(ethenylthio)-5-chloropyrimidine; 4-ethenylthio-2,3,5,6-tetrachloropyridine and similar compounds.

DETAILED DESCRIPTION OF THE INVENTION

Organic materials containing sulfur atoms have been found to have a higher refractive index than similar compounds that do not contain sulfur atoms. It is also been found that aromatic groups incorporated into organic materials increase the refractive index of the materials. However, many of the materials which incorporate sulfur and/or aromatic materials and have a high refractive index are either marginally suitable or unsuitable for use in optical communications elements (for example, optical waveguides) operating 1550 nm wavelength due to the presence of C—H bonds which strongly absorb at this wavelength. Replacing C—H bonds with C-D or C-halogen bonds can lower the C—H absorption losses. In particular, C—H absorption losses have been decreased by replacing C—H bonds with C—F bonds. However, while this replacement has decreased absorption losses, the resulting fluorine containing compound has a reduced the refractive index due to the presence of the fluorine atoms. Consequently, in order to retain the higher refractive index achieved through the use of aromatic groups and sulfur atoms; it is desirable to use organic materials in which C—H bonds are replaced by C—Cl chlorine bonds, or by a combination of C—Cl and C—F bonds.

It has been found that vinyl sulfide compounds can be used in the preparation of polymers and copolymers slated for use in optical communications applications. In particular, phenyl vinyl sulfides have been found to be advantageous because the presence of both an aromatic ring and a sulfur atom increases the refractive index of the resulting material. The aromatic vinyl sulfides compounds of the invention can be homopolymerized or can be copolymerized with other polymerizable compounds having polymerizable carbon-carbon double and triple bonds. Examples of other compounds suitable for copolymerization include other vinylic compounds including styrene compounds, acrylates, methacrylates, olefins, acetylene compounds and similar compounds, including halogenated derivatives thereof, by methods known in the art. In addition, by using a sulfur containing material in place of an oxygen containing material, the possibility of side reactions that form O—H bonds that strongly absorb at 1550 nm wavelength is avoided and the ability of the copolymer to adhere to metal surfaces, for example, gold, is increased. However, when phenyl vinyl sulfide is used, the phenyl C—H bonds contribute to the overall C—H absorbance losses. Consequently, it would be desirable to use materials in which the phenyl C—H bonds are replaced by C-halogen bonds to reduce the C—H absorbance losses.

From the foregoing, it can be seen that the use of selective highly halogenated aromatic vinyl sulfides, and corresponding highly halogenated aromatic thiols, could have great potential for the preparation of high refractive index oligomers and polymers that can be used in optical waveguides and other optical elements. Highly halogenated aromatic vinyl sulfide compounds can also be used to raise the refractive index of highly fluorinated materials that are currently under investigation for use in the preparation of optical elements such as waveguides.

While highly halogenated aromatic vinyl sulfides, and the corresponding highly halogenated aromatic thiols, offer an opportunity for preparing high refractive index materials as well as for "finishing off" polymerization reactions, such materials are not readily available. M. Kulka, *J. Org. Chem.* 24, 235–237 (1959), reported the synthesis of a variety of alkyl pentafluorophenyl sulfide compounds from chlorobenzene using alkyl mercaptans and potassium hydroxide. However, no pentachlorophenyl sulfide compounds containing S-vinyl or other S-alkenyl groups were reported. Toshihiro et al., Japanese Patent Application Publication 03-287572, reports the preparation of various vinyl sulfide compounds by the reaction of a thiol (mercaptan) compound with vinyl bromide. Included among the compounds is 1,4-bis(vinylmercapto) benzene and phenyl vinyl sulfide. In addition, Toshihiro et al. indicate that 2,3,5,6-tetrabromoxylene-α, α-dithiol as a material which can be reacted. However, no specific product was described, and any product resulting from the reaction would have a methylene group (—$CH_2$—) between the sulfur atom and the tetrabromophenylene ring. That is, the halogenated aromatic ring would not be directly bonded to the sulfur atom.

In view of the foregoing, it is desirable to prepare novel aromatic vinyl sulfide compounds in which the aromatic ring is highly halogenated. In addition, in view of the difficulties encountered utilizing the preparative methods described by Toshihiro et al is also desirable to develop a new method for preparing aromatic vinyl sulfide compounds in which the aromatic ring is highly halogenated.

The compounds of the invention include highly halogenated, halogenated-deuterated and deuterated aromatic vinyl sulfides, $A(—S—CH=CH_2)_z$, and the corresponding thiols $A-(SH)_z$, where A represents an aromatic moiety having a plurality of halogen atoms, a combination of halogen and deuterium atoms or deuterium atoms, and z is an integer in the range of 1–4 and represents the number of —S—CH=$CH_2$ groups directly attached to the aromatic ring.

As used herein, the word "aromatic" means compounds having aromaticity characteristics and includes highly halogenated, halogenated-deuterated and deuterated benzene, biphenyl and naphthalene compounds; highly halogenated, halogenated-deuterated and deuterated biphenyl ethers and thioethers; and highly halogenated, halogenated-deuterated and deuterated unsaturated 5- and 6-member heterocyclic ring systems containing carbon, at least one heteroatom selected from the group consisting of nitrogen, sulfur or oxygen. The heterocyclic rings contain carbon-carbon and/or carbon-nitrogen double bonds.

The word "highly" as used herein signifies that in addition to the —S—CH=$CH_2$ present in the compounds, all or substantially all of the hydrogen atoms attached to the ring carbon atoms of the parent compounds in any of the foregoing classes of aromatic ring compounds have been replaced by deuterium and/or halogen atoms. Replacement of "substantially all" ring carbon hydrogen atoms means that in the product aromatic vinyl sulfides of the invention, highly halogenated benzene and biphenyl rings may contain up to two hydrogen atoms per ring, naphthalene may contain two hydrogens per molecule, and heterocyclic rings may contain one hydrogen atom per ring. The preferred aromatic compounds are those which do not contain hydrogen atoms attached to the carbon atoms of the ring system, halogen and/or deuterium atoms being attached to all the carbon atoms of the ring system that are not part of the sulfide or vinyl sulfide bonds.

The halogen atoms in the highly halogenated aromatic rings include fluorine, chlorine and bromine, and mixtures thereof, attached directly to the carbon atoms of the aromatic ring. The preferred halogen atoms are fluorine and chlorine, and mixtures thereof. Particularly preferred are perchloro- and per-(chloro/deutero) aromatic rings and aromatic rings in which the number of chlorine/deuterium atoms is equal to or greater than the number of fluorine atoms. Maintaining a preponderance of chlorine and/or deuterium atoms over fluorine atoms is conducive to preparing the high refractive, low loss compounds of the invention. However, those skilled in the art will know that trade-offs can be made with regard to the relative number of chlorine/deuterium atoms and the number of fluorine atoms contained in the aromatic vinyl sulfide compounds of the invention. For example, when an aromatic ring has a plurality of attached —S—CH=CH$_2$ groups, or a combination of such attached sulfur groups and sulfur atoms within a ring system, the number of fluorine atoms on the aromatic group may exceed the number of chlorine/deuterium atoms on the ring, or only fluorine atoms may be present, without sacrificing high refractive index.

As used in all the following formulas, the subscripts a1–a6, b1–b6, c1–c6, m, n and z1–z6 are integers.

The highly halogenated, halogenated-deuterated and deuterated phenyl vinyl sulfides according to the invention are generally represented by the formula $C_6H_{a1}D_{b1}X_{c1}(—S—CH=CH_2)_{z1}$, where D is deuterium, X=F, Cl, Br and mixtures thereof, a1+b1+c1+z1=6, a1=0–3, b1=0–5, c1=0–5 and z1=1–3. The preferred compounds are those in which a1=0 and X=Cl, and those in which a1=0, b1=0, and X=Cl.

The highly halogenated, halogenated-deuterated and deuterated biphenyl vinyl sulfides according to the invention are generally represented by the formula $[C_6H_{a2}D_{b2}X_{c2}(—S—CH=CH_2)_{z2}]_2$, where D is deuterium, X=F, Cl, Br and mixtures thereof, a2+b2+c2+z2=10, a2=0–2, b2=0–8, c2=0–8, z2=2–4. The preferred compounds are those in which a2=0 and X=Cl, and those in which a2=0, b2=0, and X=Cl.

The highly halogenated, halogenated-deuterated and deuterated naphthalene vinyl sulfides according to the invention are generally represented by the formula $C_{10}H_{a3}D_{b3}X_{c3}(—S—CH=CH_2)_3$, where D is deuterium, X=F, Cl, Br and mixtures thereof, a3+b3+c3+z3=8, a3=0–2, b3=0–7, c3=1–7, and z=1–4. The preferred compounds are those in which a3=0 and X=Cl, and those in which a3=0, b3=0, and X=Cl.

The highly halogenated, halogenated-deuterated and deuterated (Ethenylthio)biphenyl ethers and thioethers according to the invention are generally represented by the formula $Y[C_6H_{a4}D_{b4}X_{c4}(—S—CH=CH_2)_{z4}]_2$, where Y=O, S, —C(CF$_3$)$_2$—, —S(O)$_2$— and —S(O)—, D is deuterium, X=F, Cl, Br and mixtures thereof, a4+b4+c4+z4=10, a4=2, b4=0–8, c4=0–8, and z4=2–4. The preferred compound are those in which a4=0 and X=Cl, and those in which a4=0, b4=0, and X=Cl.

The highly halogenated, halogenated-deuterated and deuterated heterocyclic vinyl sulfide compounds according to the invention have 5- and 6-member heterocyclic rings containing carbon and at least one heteroatom selected from the group consisting of sulfur, oxygen and nitrogen.

The 5-member heterocyclic rings are generally represented by the formula $C_4GH_{a5}D_{b5}X_{c5}(—S—CH=CH_2)_{z5}$, where G=S or O ring atoms, X=F and Cl, a5=0 or 1, b5=0–3, c5=0–3 and z5=1–3, and a5+b5+c5+z5=4. The preferred compounds are those in which a5=0 and X=Cl, and those in which a5=0, b5=0 and X=Cl.

The 6-member rings are carbon-nitrogen rings generally represented by the formula $C_mN_nH_{a6}D_{b6}X_{c6}(—S—CH=CH_2)_{z6}$, where X=F and Cl, m=3–5, n=1–3, a6=0 or 1, b6=0–4, c6=1–4, z6=1–3, and a6+b6+c6+z6=m. The preferred compounds are those in which a6=0 and X=Cl, and those in which a6=0, b6=0 and X=Cl.

Examples, without limit, of highly halogenated, halogenated-deuterated and deuterated carbon (only) ring systems, including biphenyl ethers and thioethers, that can be used to prepare the $A(—S—CH=CH_2)_z$ compounds of the invention include hexachlorobenzene; 1,2,3,4-tetrachlorobenzene; 1,2,3,5-tetrachlorobenzene; 1,2,4,5-tetrachlorobenzene; 2,3,5,6-tetrafluorobenzenedithiol; decachlorodiphenyl ether; decachlorodiphenyl thioether; 4,4'-dibromooctafluorobiphenyl; 1,4-difluoro-2,3,5,6-tetrachlorobenzene; 1,2-difluoro-3,4,5,6-tetrachlorobenzene; 1,3,5-trichlorobenzene-d$_3$; 1,4-dichlorobenzene-d$_4$; chlorobenzene-d$_5$; and similar compounds known in the art. It should be noted that deuterium containing compounds used to prepare compounds of the invention contain at least one halogen atom.

Examples, without limit, of highly halogenated heterocyclic rings that can be used to prepare the $A(—S—CH=CH_2)_z$ compounds of the invention are tetrachlorofuran; tetrachlorothiophene; tetrabromothiophene; 2,4,6-trichloro-1,3,5-triazine; 2,3,5,6-tetrachloropyrazine; 2,4,5,6-tetrachloropyrimidine; 2,3,5,6-tetrachloro-4-pyridinedithiol; 3,4,5,6-tetrachloropyridazine; 2,3,6,7-tetrachloroquinoxaline; pentachloropyridine; 3,5-dichloro-2,4,6-trifluoropyridine; 4,bromo-2,3,5,6-tetrafluoropyridine; and similar halogenated heterocyclic rings known in the art. In addition, deuterium containing analogs of any of the foregoing can be used in practicing the invention, provided that the starting compound contains at least one fluorine, chlorine or bromine atom in addition to any deuterium atoms that may be present.

In compounds of the invention, the exact value of "z" in and of the $A(—S—CH=CH_2)_z$ will be determined by the number of "reactable" halogens present on the compound used to prepare the aromatic vinyl sulfide compounds of the invention as well as the reaction conditions and amount of vinyl sulfide precursor reagent used in the reactions. Since the reactions described herein are nucleophilic aromatic ring substitutions reactions, the relative reactivity of the halogens to nucleophilic displacement is F>Cl>Br. Consequently, the reactable halogens are deemed to consist of chlorine and fluorine and typically do not include the bromine or deuterium atoms that may also be attached to the aromatic ring carbon atoms of the starting material. For example, when halogenated-deuterated compounds are used to prepare the compounds of the invention, such compounds must contain at least one chlorine or fluorine atom. When fluoro-chloro and fluoro-bromo compounds are used to prepare the compounds of the invention, the fluorine can be displaced before the chlorine or bromine. Thus, one mole of 4,4'-dibromooctafluorobiphenyl, reacting with approximately two moles of 2-mercaptoethanol and followed by further reactions in accordance with the Examples herein, would yield 3,3'-bis(ethenylthio)-4,4'-dibromohexafluorobiphenyl as the product. Other mechanisms such as E2 elimination leading to benzyne intermediates may remove the bromo or chloro atoms in preference to fluorine. However, the expected products of this mechanism will be very different from the desired products.

Examples, without limit, of compounds of the invention containing more than one —S—CH=CH$_2$ moiety include 1,4-bis(ethenylthio)-2,3,5,6-tetrachlorobenzene; 2,4,6-tris (ethenylthio)-1,3,5-triazine; 4,4'-bis(ethenylthio)biphenyl; 4,4'-bis(ethenylthio)biphenyl ether; 4,4'-bis(ethenylthio) biphenyl thioether; 1,4-bis(ethenylthio)benzene-d$_4$; isomers of bis-ethenylthio)-hexafluoronapthalene; isomers of tris (ethenylthio)-pentafluoronapthalene; isomers of tetrakis (ethenylthio)-tetrafluoronapthalene; and similar compounds in accordance with the foregoing paragraphs.

Initially, attempts were made to prepare highly halogenated compounds as disclosed herein using the method of Toshihiro et al., Japanese Patent Application Publication 03–287572. In order to determine whether the Toshihiro method would work to make aromatic vinyl sulfides in which the aromatic ring was halogenated, the preparation of bromophenyl vinyl sulfide was chosen as a model compound. Toshihiro et al. prepared phenyl vinyl sulfide, but not the brominated species by the reaction, under pressure, of thiophenol with vinyl bromide using potassium hydroxide (KOH) in dimethylformamide (DMF) solution. The present inventors carried out the same experiment, except that 4-bromotiophenol was used in place of thiophenol. All experimental attempts to prepare 4-bromophenyl vinyl sulfide by this method failed, yielding different yet consistent results. The products consisted of either one major compound the disulfide dimer (4-BrC$_6$H$_4$S)$_2$, or a mixture of oligomers. A method for the preparation of 4-bromophenyl vinyl sulfide which did succeed was based on that used by F. W. Harris and J. Rizzo, Polymer 41 (2000) 5125–5136, to synthesize trifluorovinyl ethers.

Preparation of 4-bromophenyl vinyl ether (1)

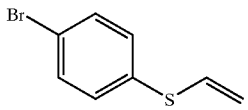

(1)

4-Bromothiophenol (1.0 g, 5.29 mmol) was dissolved in DMSO (20 ml) and toluene (10 ml), and potassium hydroxide (0.38 g, 1.1 eq) was added. The mixture was stirred under reflux for 2 hr. with removal of water through a Dean-Stark trap. The potassium salt thus generated was not isolated, but used in solution. The mixture was allowed to cool, and 1-bromo-2-chloroethane (1.52 g, 2 eq) was added to the salt solution to form the S-bonded 2-chloroethyl intermediate. After stirring for 1 h, the solution was treated with the dropwise addition of potassium-t-butoxide (5.8 ml of a 1.0 M solution in THF), maintaining the temperature below 40° C., to eliminate HCl and form the vinylic compound. Saturated ammonium chloride solution was added and the organic phase was isolated and combined with the ether layers from three aqueous phase extractions. The combined organic layers were dried over anhydrous magnesium sulfate and evaporated to give a yellow oil (0.77 g, 68%). GC-MS analysis of the crude product indicated that the desired 4-bromophenyl vinyl sulfide had been formed as the major product, with only the unreacted intermediate alkyl halide as a minor by-product. The material was not purified.

In the above synthesis, the formation of the potassium salt was straightforward and the bromochloroethane could be added to the mixture in one portion since it was very unlikely that the sulfide ion would react with the chloro end to form a dimer. The reaction mixture remained in solution throughout the experiment and the elimination of HCl to form the vinylic group was carried out in situ using the potassium tert-butoxide.

Once 4-bromophenyl vinyl sulfide was prepared, attempts were made to prepare 1,4-bis(ethenylthio)-2,3,5,6-tetrachlorobenzene, 1,4-(CH$_2$=CHS)$_2$C$_6$Cl$_4$, by reaction of 2,3,5,6-tetrachlorobenzenedithiol with 1-bromo-2-chloroethane using the same procedures as above, However, since the dithiol compound is bifunctional as is 1-bromo-2-chloroethane, it was anticipated that more by-products would be formed. Initial experiments following the above procedures indicated that it might be preferable to isolate and purify the chloroethane intermediate before proceeding with the dehydrohalogenation step since the reaction to produce the intermediate compound is not clean and any impurities, especially if they are reactive, tend to be magnified during the dehydrohalogenation step. The best quality chlorinated intermediate, 1,4-bis(2-chloroethylthio) benzene, is obtained after hot extraction, filtration and recrystallization from chloroform. The structure was confirmed by GC-MS. The intermediate was not particularly soluble in solvents suitable for dehydrohalogenation using potassium tert-butoxide, being completely soluble only in dilute solutions. Consequently, the dehydrohalogenation was carried out as a suspension of the intermediate. While dehydrohalogenation with potassium tert-butoxide gave the best results, the 1,4-bis(ethenylthio)-2,3,5,6-tetrachlorobenzene product was never produced or isolated cleanly, or in good yield. Decomposition, evidenced by darkening of the reaction mixture, was often observed. The product prepared by this method was deemed unsuitable for use in making optical elements, for example, optical waveguides. A modification of this procedure is described below in Examples (i) and (ii).

Hexachlorobenzene has been reported in the literature to undergo nucleophilic substitution at the 1,4-positions with alkyl mercaptides [*J. Org. Chem.* 24 (1959), 235–237] In particular, reaction with mercaptoethanol was shown to give the p-hydroxyethylmercapto derivative. This procedure was therefore used as the first step in a new approach to the synthesis of tetrachlorobenzene divinyl sulfide [a.k.a. 1,4-bis(ethenylthio)-2,3,5,6-tetrachlorobenzene]. The reaction was straightforward to give the diol as a clean single product in good yield. It was unlikely that the elimination to give the divinyl sulfide derivative would occur readily via direct dehydration of the primary alcohol since the intermediate carbocation would be unstable. This type of dehydration occurs readily with tertiary alcohols. Therefore, a way of approaching this step was to make a derivative of the alcohol, which could then be eliminated more easily. Synthesis of a tosyl derivative was not accomplished readily. Synthesis of an acetate derivative was carried out simply by refluxing in acetic anhydride. However, this derivative proved to be very stable and did not undergo elimination.

The chloride derivative was produced very simply by refluxing the diol in thionyl chloride. The structure of this chloride is in fact identical to the material obtained by reaction of tetrachlorobenzenedithiol with 1-bromo-2-chloroethane via a sulfide anion intermediate. The one major difference was the quality of the product: the second route yielded a far superior material. This was evidenced by its melting point, TLC analysis and even appearance, and proved to be a significant factor for the subsequent elimination. The 1,4-bis(ethenylthio)-2,3,5,6-tetrachlorobenzene resulting from this synthesis was suitable for use in the manufacturing of optical elements, for example, optical waveguides.

The reactions pathways for preparing 1,4-bis(ethenylthio)-2,3,5,6-tetrachlorobenzene from 2,3,5,6-tetrachlorobenzenedithiol or hexachlorobenzene shown below.

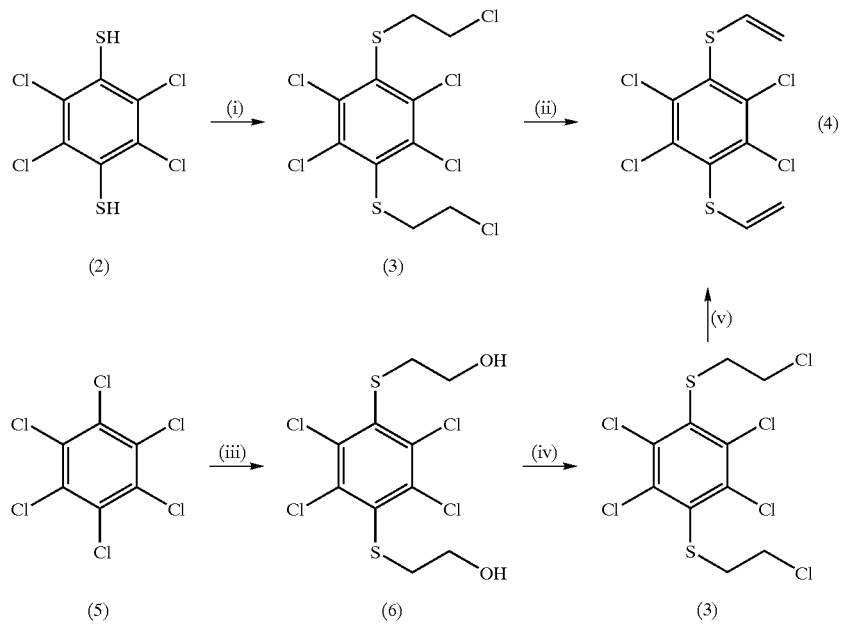

EXAMPLE (i)

Synthesis of 1,4-bis (2-chloroethylthio)-2,3,5,6-tetrachlorobenzene (3) from 2,3,5,6-tetrachlorobenzenedithiol The starting material, tetrachlorobenzenedithiol (8) was synthesized in-house in three steps from tetrachlorohydroquinone. Tetrachlorobenzenedithiol (10.0 g, 35.7 mmol) was dissolved in DMSO (100 ml) and toluene (50 ml), and potassium hydroxide (5.2 g, 2.2 eq) was added. The mixture was stirred under reflux for 14 h with removal of water through a Dean-Stark trap. Since the potassium salt thus obtained was very insoluble, the mixture was added as small solid portions, with rapid stirring, to a round bottom flask containing 1-bromo-2-chloroethane (11.3 g, 78.5 mmol). After the addition was complete, the mixture was stirred at room temperature for 4 hr., washed with water and extracted with dichloromethane. The organic solution was dried over anhydrous magnesium sulfate, filtered and concentrated to give a sticky dark brown solid. Recrystallization (hot filtration) from chloroform gave the title adduct as a tan crystalline solid (8.6 g, 59%).

EXAMPLE (ii)

Synthesis of 1,4-bis(ethenylthio)-2,3,5,6-tetrachlorobenzene (3) from 1,4,-bis(2-chloroethylthio)-2,3,5,6-tetrachlorobenzene Prepared in Example (i)

A suspension of (9) (100 mg, 0.25 mmol) in THF was stirred rapidly while potassium tert-butoxide (0.6 ml of a 1.0 M solution in THF) was added dropwise. Saturated ammonium chloride solution was added after 10 min., the organic phase was isolated and combined with the ether layers from three aqueous phase extractions. The combined organic layers were dried over anhydrous magnesium sulfate and evaporated to give a dark yellow oil. GC-MS analysis of the crude product indicated that the divinyl sulfide had been formed as the major compound, with several minor by-products. The material was not purified.

EXAMPLE (iii)

Synthesis of 1,4-bis(2-hydroxyethylthio)-2,3,5,6-tetrachlorobenzene (6) from Hexachlorobenzene To a stirred suspension of hexachlorobenzene (50.0 g, 0.18 mol), pyridine (175 ml) and methanol (35 ml), was added dropwise a solution of potassium hydroxide (24.3 g, 0.36 mol), 2-mercaptoethanol (28 ml) and methanol (18 ml) over a period of 30 min. The temperature was maintained at 65–68° C. by occasional cooling. The reaction mixture was then stirred for an additional hour, let stand overnight and then filtered. The filtrate was concentrated to a volume of about 60 ml, boiling methanol (60 ml) was added, and the solution allowed to cool. The white precipitate was filtered, washed with methanol and dried. Recrystallization from methanol gave the title product as a white crystalline solid in two crops (41 g, 64%), (mp. 149–152° C., lit. 151–153° C.).

EXAMPLE (iv)

Synthesis of 1,4-bis(2-chloroethylthio)-2,3,5,6-tetrachlorobenzene (3) from -bis(2-hydroxyethylthio)-2,3,5,6-tetrachlorobenzene of Example (iii)

A mixture of (12) (40 g, 0.11 mol) and thionyl chloride (300 ml) was heated under reflux for 4 h and stirred at room temperature overnight. The precipitated product was filtered, washed with methylene chloride and dried (39 g, 89%), (mp. 173–178° C., lit. 175–179° C.). The filtrate was concentrated on a rotary evaporator and the residue was recrystallized from toluene to give a small second crop of the alkyl halide.

EXAMPLE (v)

Synthesis of 1,4-bis(ethenylthio)-2,3,5,6-tetrachlorobenzene (4) from 1,4-bis(2-chloroethylthio)-2,3,5,6-tetrachlorobenzene of Example (iv)

To a rapidly stirring suspension of compound (9) (30 g, 74 mmol) in methylene chloride (300 ml) was added dropwise a solution of 1,8-diazabicyclo[5.4.0]undec-7-ene (25 g, 164 mmol) in methylene chloride (100 mL). The mixture was then heated at 40° C. for 24 hr. and stirred at room temperature for 48 hr. The precipitated product was filtered, washed with hexane and dried. The filtrate was concentrated and filtered to yield a second crop of material (20 g, 74% combined).

The filtrate may be worked up to yield a third crop of slightly impure product: 1.0 M ammonium hydroxide solution was added to the filtrate that was washed and separated. The aqueous layer was extracted with methylene chloride, and the organic fractions were combined, washed with water and dried over anhydrous magnesium sulfate. After filtering, the solution was concentrated to give a very pale yellow solid (5.5 g, 20%).

EXAMPLE (vi)

Preparation of 2,4,6-tris(ethenylthio)-1,3,5-triazine

A solution of 2,4,6-trichloro-1,3,5-triazine in pyridine is treated in a dropwise manner with a solution of potassium hydroxide, a molar excess (based on Cl) of 2-mercaptoethanol and methanol over a period of 30 min. The temperature is maintained at 65–68° C. by occasional cooling. The reaction mixture is then stirred for an additional hour and filtered. The filtrate is then concentrated, hot methanol is added, and the solution is allowed to cool. The precipitated product, 2,4,6-tris(ethenylthio)-1,3,5-triazine, is recrystallized from pyridine/methanol.

In an alternate procedure, 2,4,6-tris(ethenylthio)-1,3,5-triazine is prepared in accordance with Examples (i) and (ii) starting from 1,3,5-triazine-2,4,6-trithiol.

The foregoing non-limiting examples serve to illustrate the invention. It will be apparent to those skilled in the art that various modifications and variations can be made to the present invention without departing from the spirit and scope of the invention. For example, changes in proportions and alternatives in starting materials will be may be used to prepare aromatic vinyl sulfides similar to those described herein. Thus it is intended that the present invention cover the modifications and variations provided then come within the scope of the appended claims and their equivalents.

What is claimed is:

1. Aromatic vinyl sulfide compounds of formula $A(-S-CH=CH_2)_z$,
   wherein z is an integer in the range of 1–4 and A is selected from the group consisting of halogenated, halogenated-deuterated and deuterated biphenyl and naphthalene compounds; halogenated, halogenated-deuterated and deuterated biphenyl ethers and thioethers; and halogenated, halogenated-deuterated and deuterated unsaturated 5- and 6-member heterocyclic ring systems containing carbon and at least one heteroatom selected from the group consisting of nitrogen, oxygen and sulfur; and
   wherein $A(-S-CH=CH_2)_z$ is a biphenyl vinyl sulfide compound of formula: $[C_6H_{a2}D_{b2}X_{c2}(-S-CH=CH_2)_{z2}]_2$, wherein D is deuterium, X=F, Cl, Br and mixtures thereof, a2+b2+c2+z2=10, a2=2, b2=0–8, c2=0–8, and z2=2–4.

2. The compounds according to claim 1, wherein a2=0 and X=Cl.

3. The compounds according to claim 1, wherein a2=0, b2=0 and X=Cl.

4. Aromatic vinyl sulfide compounds of formula $A(-S-CH=CH_2)_z$,
   wherein z is an integer in the range of 1–4 and A is selected from the group consisting of halogenated, halogenated-deuterated and deuterated biphenyl and naphthalene compounds; halogenated, halogenated-deuterated and deuterated biphenyl ethers and thioethers; and halogenated, halogenated-deuterated and deuterated unsaturated 5- and 6-member heterocyclic ring systems containing carbon and at least one heteroatom selected from the group consisting of nitrogen, oxygen and sulfur; and
   wherein $A(-S-CH=CH_2)_z$ is a naphthalene compound of formula: $C_{10}H_{a3}D_{b3}X_{c3}(-S-CH=CH_2)_{z3}$, wherein D is deuterium, X=F, Cl, Br and mixtures thereof; a3+b3+c3+z3=8, a3=0–2, b3=0–7, c3=1–7, and z3=1–4.

5. The compounds according to claim 4, wherein a3=0 and X=Cl.

6. The compounds according to claim 4, wherein a3=0, b3=0 and X=Cl.

7. Aromatic vinyl sulfide compounds of formula $A(-S-CH=CH_2)_z$,
   wherein z is an integer in the range of 1–4 and A is selected from the group consisting of halogenated, halogenated-deuterated and deuterated biphenyl and naphthalene compounds; halogenated, halogenated-deuterated and deuterated biphenyl ethers and thioethers; and halogenated, halogenated-deuterated and deuterated unsaturated 5- and 6-member heterocyclic ring systems containing carbon and at least one heteroatom selected from the group consisting of nitrogen, oxygen and sulfur; and
   wherein $A(-S-CH=CH_2)_z$ is a biphenyl ether and thioether vinyl sulfide compound of formula $Y[C_6H_{a4}D_{b4}X_{c4}(-S-CH=CH_2)_{z4}]_2$, wherein Y=O, S, $-C(CF_3)_2-$, $-S(O)_2-$ and $-S(O)-$, D is deuterium, X=F, Cl, Br and mixtures thereof; a4+b4+c4+z4=10, a4=2, b4=0–8, c4=0–8, and z4=2–4.

8. The compounds according to claim 7, wherein a4=0 and X=Cl.

9. The compounds according to claim 7, wherein a4=0, b4=0 and X=Cl.

10. Aromatic vinyl sulfide compounds of formula $A(-S-CH=CH_2)_z$,
    wherein z is an integer in the range of 1–4 and A is selected from the group consisting of halogenated, halogenated-deuterated and deuterated biphenyl and naphthalene compounds; halogenated, halogenated-deuterated and deuterated biphenyl ethers and thioethers; and halogenated, halogenated-deuterated and deuterated unsaturated 5- and 6-member heterocyclic ring systems containing carbon and at least one heteroatom selected from the group consisting of nitrogen, oxygen and sulfur; and
    wherein $A(-S-CH=CH_2)_z$ is a 5-member heterocyclic ring containing compounds of formula $C_4GH_{a5}D_{b5}X_{c5}(-S-CH=CH_2)_{z5}$, wherein G=S or O ring atoms, X=F, Cl and mixtures thereof, a5=0 or 1, b5=0–3, c5=0–3 and z5=1–3, and a5+b5+c5+z5=4.

11. The compounds according to claim 10, wherein a5=0 and X=Cl.

12. The compounds according to claim 10, wherein a5=0, b5=0 and X=Cl.

13. Aromatic vinyl sulfide compounds of formula $A(-S-CH=CH_2)_z$, wherein z is an integer in the range of 1–4 and A is selected from the group consisting of halogenated, halogenated-deuterated and deuterated biphenyl and naphthalene compounds; halogenated, halogenated-deuterated and deuterated biphenyl ethers and thioethers; and halogenated, halogenated-deuterated and deuterated unsaturated 5- and 6-member heterocyclic ring systems containing carbon and at least one heteroatom selected from the group consisting of nitrogen, oxygen and sulfur; and wherein $A(-S-CH=CH_2)_z$ is a 6-member heterocyclic ring containing compounds of formula $C_mN_nH_{a6}D_{b6}X_{c6}(-S-CH=CH_2)_{z6}$, wherein X=F, Cl and mixtures thereof, m=3–5, n=1–3, a6=0 or 1, b6=0–4, c6=1–4, z6=1–3, and a6+b6+c6+z6=m.

14. The compounds according to claim 13, wherein a6=0 and X=Cl.

15. The compounds according to claim 13, wherein a6=0, b6=0 and X=Cl.

16. The biphenyl vinyl sulfide compounds according to claim 1, wherein said compounds are selected from the group consisting of 4,4'-bis(ethenylthio)-2,2',3,3',5,5',6,6'-octachlorobiphenyl and nonachlorobiphenyl vinyl sulfide.

17. The naphthalene vinyl sulfide compounds according to claim 4, wherein said compounds are selected from the group consisting of isomers of bis-ethenylthio)-hexafluoronapthalene, isomers of tris(ethenylthio)-pentafluoronapthalene, isomers of tetrakis(ethenylthio)-tetrafluoronapthalene.

18. The biphenyl ether and thioethers compounds according to claim 7, wherein said compounds are selected from the group consisting of and 4,4'-bis(ethenylthio)-2,2',3,3',5,5',6,6'-octachlorobiphenyl thioether and 4,4'-bis(ethenylthio)-2,2',3,3',5,5',6,6'-octachlorobiphenyl ether.

19. The 5-member heterocyclic ring compounds according to claim 10, wherein said compounds are selected from the group consisting of 4-bis(ethenylthio)-2,5-dichlorofuran; 2,5-bis(ethenylthio)-2,4-dichlorofuran; 2,3,4,5-tetrakis(ethenylthio)furan; 3,4-bis(ethenylthio)-2,5-dichlorothiofuran; 2,5-bis(ethenylthio)-2,4-dichlorothiofuran; 2,3,4,5-tetrakis(ethenylthio)thiofuran.

20. The 6-member heterocyclic ring compounds according to claim 13, wherein said compounds are selected from the group consisting of 4-ethenylthio-2,6-dichloro-1,3,5-triazine; 2,4,6-tris(ethenylthio)1,3,5-triazine; 2,6-bis(ethenylthio)-3,5-dichloropyrazine; 2,3,5,6-tetrakis(ethenylthio)pyrazine; 4,6-bis(ethenylthio)-2,5-dichloropyrimidine; 2,4,6-tris(ethenylthio)-5-chloropyrimidine; 4-ethenylthio-2,3,5,6-tetrachloropyridin.

* * * * *